US00PP20221P3

(12) United States Plant Patent
Ferrero

(10) Patent No.: US PP20,221 P3
(45) Date of Patent: Aug. 18, 2009

(54) ***MUSSAENDA* PLANT NAMED 'MARMALADE'**

(50) Latin Name: ***Mussaenda* hybrid**
Varietal Denomination: Marmalade

(75) Inventor: Michael D. Ferrero, Cairns (AU)

(73) Assignee: Bloomin' Good, Inc., Homestead, FL (US)

( * ) Notice: Subject to any disclaimer, the term of this patent is extended or adjusted under 35 U.S.C. 154(b) by 71 days.

(21) Appl. No.: 11/983,272

(22) Filed: Nov. 8, 2007

(65) Prior Publication Data

US 2008/0127381 P1 May 29, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Susan B McCormick Ewoldt
(74) *Attorney, Agent, or Firm*—Jondle & Associates, P.C.

(57) ABSTRACT

A new *Mussaenda* plant particularly distinguished by its prominent, bright yellow flowers with a yellow-orange eye which ages from orange to brown, trapezoidal sepals which range in color from bright yellow to orange to pink and red-purple, and sepals which are pendulous and are occasionally twisted. Additionally, this mew *Mussaenda* plant can withstand brief periods of freezing temperatures without damage.

1 Drawing Sheet

Genus and species: *Mussaenda* hybrid.
Variety denomination: 'Marmalade'.

BACKGROUND OF THE NEW PLANT

The present invention comprises a new and distinct cultivar of *Mussaenda,* botanically known as *Mussaenda* hybrid, and hereinafter referred to by the cultivar name 'Marmalade'. The new cultivar originated from a hybridization made in December 1995 in Alipore, India. The female parent was the hot-pink-flowered *Mussaenda philippica* plant 'Doña Luz' (unpatented), while the male parent was a pale-yellow-flowered individual plant of *Mussaenda luteola* (unpatented). The seeds produced by the hybridization were sown in 1996 in Alipore, India and a single plant selection was chosen for further evaluation and for asexual propagation in 1998/1999 in Alipore, India.

The new cultivar was created in 1995 in Alipore, India and has been asexually reproduced repeatedly by vegetative cuttings and tissue culture in Homestead, Florida over a two-year period. The present invention has been found to retain its distinctive characteristics through successive asexual propagations.

SUMMARY OF THE INVENTION

The following are the most outstanding and distinguishing characteristics of this new cultivar when grown under normal horticultural practices in Homestead, Fla.

1. Flowers are prominent, bright yellow with a yellow-orange eye which ages from orange to brown;
2. Trapezoidal sepals range in color from bright yellow to orange to pink and red-purple;
3. Sepals are pendulous and are occasionally twisted; and
4. Can withstand brief periods of freezing temperatures without damage.

DESCRIPTION OF THE PHOTOGRAPHS

This new *Mussaenda* plant is illustrated by the accompanying photographs which show blooms, buds, and foliage of the plant; the colors shown are as true as can be reasonably obtained by conventional photographic procedures.

DESCRIPTION OF THE NEW CULTIVAR

Figure 1:
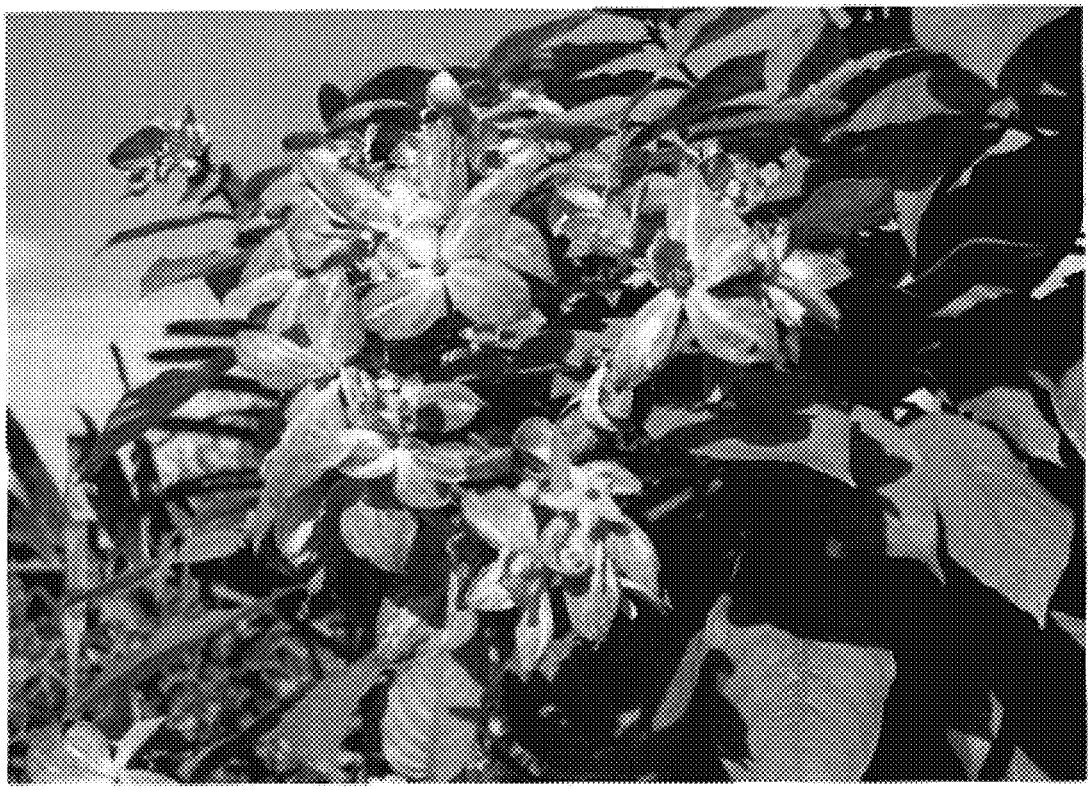
FIG. 1 shows a cluster of flowers and leaves on a 2-year-old plant.
Figure 2:
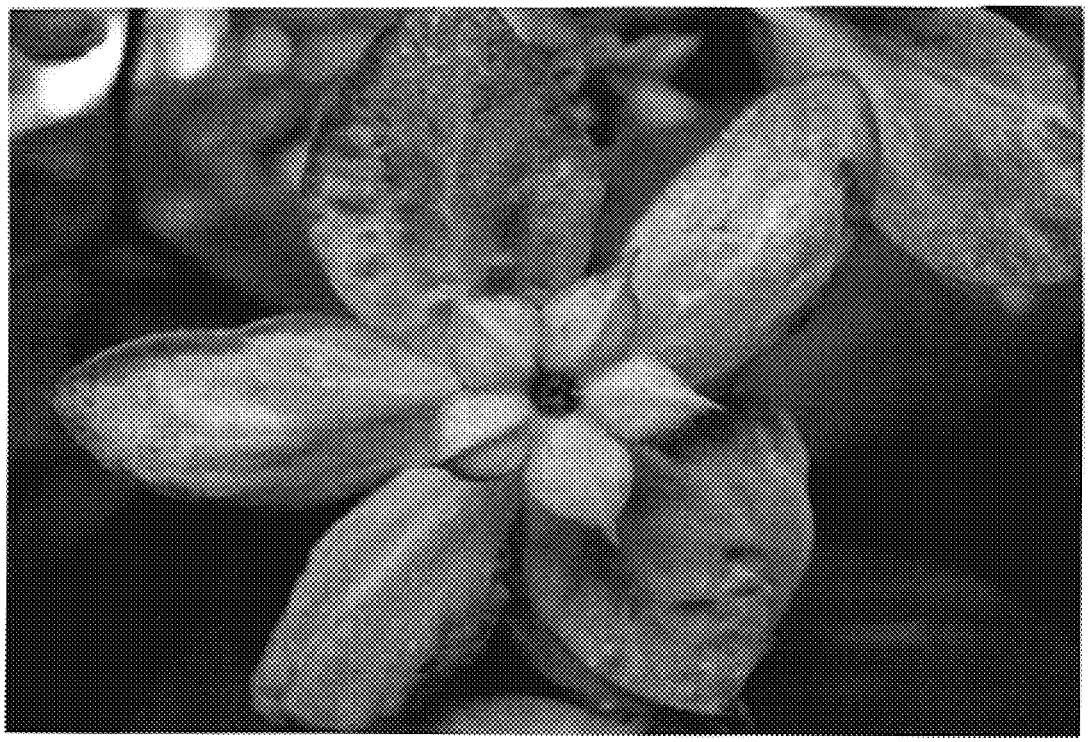
FIG. 2 shows a close-up of a single flower.

The following detailed descriptions set forth the distinctive characteristics of 'Marmalade'. The data which define these characteristics were collected from asexual reproductions carried out in Homestead, Fla. The plant history was taken on six-month-old plants grown in 10-gallon containers. Color readings were taken in under natural light. Color references are primarily to the R.H.S. Colour Chart of The Royal Horticultural Society of London (R.H.S.) (2001 edition).

DESCRIPTION OF THE NEW PLANT

Classification:
*Family.*—Rubiaceae.
*Botanical name.*—*Mussaenda* hybrid.
Parentage:
*Female parent.*—*Mussaenda philippica.*—'Dona Luz' (unpatented).
*Male parent.*—An individual unnamed plant of *Mussaenda luteola* (unpatented).
Growth:
*Type.*—Tropical shrub; tender perennial.
*Form.*—Upright with many branches, soft wood, terminating in velvet-like soft foliage.

*Habit.*—Compact, multi-branched, non-suckering from base, hard wood trunk, new growth soft and flexuous, hardening off after some time.

*Height.*—About 2.44 m at two-years-old.

*Diameter* (*spread*).—2 m.

*Time to initiate and develop roots* (*days or weeks*).—Air layers about 2 months; tip cuttings about 3 weeks.

*Propagation.*—Air layering and tip cuttings.

*Root description.*—Fibrous, freely branching, and white.

Branches:

*New growth.*—Length: 27 cm to 30 cm. Diameter: 0.3 cm at midpoint. Color: RHS 144A. Texture: Pubescent; hairs about 0.15 cm long.

*Six-months-old.*—Length: 9 cm from soil line to first node. Diameter: 0.9 cm at midpoint between soil line and first node. Internode length: 3.0 cm to 4.0 cm. Color: RHS 199B. Texture: Woody, smooth.

Leaves:

*Immature.*—Length: 2.6 cm to 3.7 cm. Width: 1.0 cm to 1.6 cm. Shape of leaf: Lanceolate. Apex: Cuspidate. Base: Shortly attenuate. Margin: Entire. Texture: Pubescent on both surfaces. Pubescence color: RHS 60A on mid-rib on lower surface otherwise RHS N155A. Leaf Color: Upper surface: RHS 137A. Lower surface: RHS 146B.

*Mature.*—Length: 17.0 cm to 19.7 cm. Width: 7.6 cm to 8.9 cm. Shape of leaf: Lanceolate. Apex: Cuspidate. Base: Attenuate. Margin: Entire. Texture: Pubescent. Pubescence distribution: Both surfaces of the leaf are covered in very small hairs which make the leaf feel very soft; the lower surface has more hairs on the mid-rib and veins than on the rest of the leaf. Pubescence length: 0.1 cm on mid-rib and veins of lower surface; 0.05 cm on rest of leaf. Pubescence color: RHS N155A. Leaf Color: Upper surface: RHS 137A to RHS 137C. Lower surface: RHS 138B. Venation: Pinnate. Venation color: Upper surface: RHS 137A to RHS 137C. Lower surface: RHS 145C.

*Petiole.*—Length: 1.0 cm Diameter: 0.2 cm to 0.3 cm. Color: RHS 137C to RHS 138B. Texture: Pubescent.

Flowers:

*Type.*—Corymb.

*Blooming habit.*—In bloom 7 months of the year, from late Spring until late Fall.

*Lastingness of individual blooms on the plant.*—Flowers last about 4 days while sepals last about 10 weeks.

*Fragrance.*—Absent.

*Time of flowering* (*time of year or months*).—Flowers March to November.

*Length of flowering period.*—7 to 8 months.

*Total length, from pedicel attachment to top of opened petals of a fully opened flower.*—2.7 cm to 3.5 cm. Width, from sepal tip to sepal tip of fully opened flower: 8.0 cm to 8.5 cm Flower buds (as sepals are starting to open):

*Shape.*—Orbicular.

*Length.*—0.8 cm.

*Diameter.*—0.8 cm as measured across the top where the sepals are opening.

*Color.*—RHS 138B.

*Texture.*—Pubescent.

*Pubescence color.*—RHS 60A on bottom half of bud and on the pedicel where it joins the bud; RHS N155A on upper half of bud.

Flower buds (sepals partially open):

*Shape.*—Trullate with slight ribbing lengthwise.

*Length.*—0.5 cm.

*Diameter.*—0.3 cm at widest point.

*Depth from pedicel attachment to tip of bud.*—1.1 cm.

*Color.*—RHS 144B.

*Texture.*—Densely pubescent.

*Pubescence color.*—RHS N155A with RHS 60A at the tips

*Sepals.*—Shape: Cordate. Apex: Apiculate. Base: Fused. Margin: Entire. Length from bud attachment to tip of sepal: 0.7 cm. Width: 0.5 cm. Width from sepal tip to sepal tip: 1.5 cm. Color: Upper surface: RHS 144B with RHS N30B at the tip. Lower surface: RHS 144B. Texture: Pubescent.

Flower buds (sepals fully open):

*Shape.*—Orbicular with prominent ribs.

*Length.*—1.3 cm.

*Diameter.*—0.4 cm at widest point.

*Color.*—RHS 138C.

*Texture.*—Densely pubescent.

*Pubescence color.*—RHS N155A from pedicel attachment to 0.8 cm; RHS 63B remaining 0.5 cm.

Flowers (fully opened, excluding sepals):

*Shape.*—Umbrella-shaped consisting of 5 petals with the bases fused to form a long tube; each petal has a prominent ridge on the upper surface extending from near the center of the flower to the tip of each petal running the length of the petal.

*Size.*—Diameter, from petal tip to petal tip: 2.1 cm. Depth, from top of petals to top of sepals: 2.0 cm.

*Petals.*—Shape: Cordate. Length, from center of flower to petal tip: 1.0 cm. Width, at widest point: 0.7 cm. Apex: Apiculate. Base: Fused. Margin: Entire. Color: Upper surface: RHS 17A; RHS N30B where the petals fuse together. Lower surface: RHS N 155B with RHS 63B veins and margins. Outer surface of corolla tube: RHS 63B; RHS 145C where the tube meets the sepals. Texture: Pubescent, very short upright hairs cover both surfaces and make the surface appear to sparkle; dense longer hairs located at the center of the corolla forming a central "eye". Pubescence color: RHS 22A at the throat (eye) of the corolla tube, continuing down into the tube and surrounding the reproductive organs; dense pubescence of RHS 44B occurs in a ring just outside the throat of the corolla tube.

Sepals:

*Shape.*—Trapezoidal.

*Apex.*—Apiculate, point at tip of sepal lengthens as sepals age, from less than 0.1 cm to 1.0 cm.

*Base.*—Fused to form a long tube.

*Margin.*—Entire.

*Immature sepals* (*when flower is open*).—Length, from throat of tube to tip of sepal: 1.7 cm to 2.5 cm. Width: 1.0 cm to 1.3 cm. Texture: Upper surface: Pubescent, very short fine hairs which make the surface appear to sparkle. Lower surface: Pubescent; more hairs along the veins; pubescence of RHS 60A on the veins. Color: Upper surface: Patches and streaks of RHS 21A, RHS 3A but brighter, RHS 31A to RHS 31B with RHS 60B at the tip. Lower surface: RHS 157A. Outer sepal tube: From pedicel attachment to 1.0 cm RHS 144A with dense RHS 63A pubescence; from 1 cm above pedicel attachment to top of tube RHS 145A to RHS 145B with light RHS 63A pubescence.

*Mature sepals.*—Length, from throat of tube to tip of sepal: 4.0 cm to 4.5 cm. Width: 2.8 cm to 3.0 cm. Texture: Upper surface: Pubescent, very short upright hairs which make the surface appear to sparkle. Lower surface: Pubescent; more hairs along the veins; pubescence RHS 60A. Color: Upper surface: Base color of RHS 3A but brighter with patches and streaks of RHS 63B, RHS N66B to RHS N66C, RHS 33A to RHS 34A; where the sepal bases fuse together and surrounding the corolla tube of the inserted flower, there is heavy pubescence of RHS 46A which extends down into the throat of the sepal tube. Lower surface: RHS 158C at base RHS 134B with RHS 142B in the middle and RHS 142A at the tip. Outer sepal tube: From pedicel attachment to 1.0 cm RHS 144A with dense RHS 63A pubescence; from 1 cm above pedicel attachment to top of tube RHS 145A to RHS 145B with light RHS 63A pubescence. Venation: Type: Pinnate. Color: Upper surface: Indistinct. Lower surface: Some veins are RHS 63B and some veins are RHS 199C.

*Pedicels.*—Length: Varies from 1.5 cm to 7.0 cm. Diameter: 0.1 cm to 0.2 cm. Texture: Pubescent; hairs RHS N155A. Color: RHS 144A.

Reproductive organs:

*Pistils.*—Number: 1. Length: 1.8 cm.

*Style.*—Length: 1.2 cm. Diameter: Less than 0.1 cm. Color: RHS N144D.

*Stigmans.*—Shape: Bifurcate. Length: 0.4 cm. Color: RHS N144D.

*Stamens.*—Number 5. Length: 1.3 cm. Diameter: Less than 0.1 cm. Color: Near RHS 199B.

*Pollen.*—None; sterile hybrid.

Fruit and seed set: 'Marmalade' is a sterile hybrid and does not produce fruit, seed or false seed pods.

Disease and insect resistance: 'Marmalade' appears to be resistant to many insect pests and can withstand brief periods of freezing temperatures without damage.

COMPARISON WITH PARENTAL CULTIVARS

'Marmalade' differs from the female parent, 'Doña Luz' (unpatented) in that 'Marmalade' has sepals which emerge yellow especially when shaded and become orange in full sun and as they age, whereas 'Doña Luz' has sepals which emerge hot pink and stay the same color as they age. Additionally, 'Marmalade' has a prominent bright yellow-orange "eye" while 'Doña Luz' has a smaller, light yellow-orange "eye". Finally, 'Marmalade' has sepals which are trapezoidal, pendulous and often twisting, whereas 'Doña Luz' has sepals which are oval, do not twist and are evenly uniform in shape.

'Marmalade' differs from the male parent, *Mussaenda luteola* (unpatented) in that 'Marmalade' has sepals which emerge yellow especially when shaded and become orange in full sun and as they age, whereas *M. luteola* has sepals which emerge pale yellow and stay the same color as they age. Additionally, 'Marmalade' has star-shaped flowers with a prominent yellow orange eye, whereas *M. luteola* has salver-shaped flowers with a small orange eye. Finally, 'Marmalade' has sepals which are trapezoidal, pendulous, often twisting and arranged haphazardly around each flower, whereas *M. luteola* has sepals which are pennant-shaped, numerous and arranged in a neat even cluster around each flower.

I claim:

1. A new and distinct cultivar of *Mussaenda* plant as shown and described herein.

* * * * *